United States Patent
Tsutsui et al.

(10) Patent No.: US 10,877,021 B2
(45) Date of Patent: Dec. 29, 2020

(54) DEVICE FOR BIOLOGICAL MATERIAL DETECTION, DETECTION APPARATUS FOR BIOLOGICAL MATERIAL DETECTION, METHOD FOR MEASURING ION CURRENT, AND METHOD FOR IDENTIFYING BIOLOGICAL MATERIAL

(71) Applicants: OSAKA UNIVERSITY, Osaka (JP); TOKYO INSTITUTE OF TECHNOLOGY, Tokyo (JP); NATIONAL UNIVERSITY CORPORATION TOKYO MEDICAL AND DENTAL UNIVERSITY, Tokyo (JP)

(72) Inventors: Makusu Tsutsui, Osaka (JP); Kazumichi Yokota, Osaka (JP); Masateru Taniguchi, Osaka (JP); Tomoji Kawai, Osaka (JP); Mina Okochi, Tokyo (JP); Masayoshi Tanaka, Tokyo (JP); Yoshinobu Baba, Aichi (JP); Noritada Kaji, Aichi (JP); Takao Yasui, Aichi (JP); Yuji Miyahara, Tokyo (JP); Yukichi Horiguchi, Tokyo (JP)

(73) Assignees: OSAKA UNIVERSITY, Osaka (JP); TOKYO INSTITUTE OF TECHNOLOGY, Tokyo (JP); NATIONAL UNIVERSITY CORPORATION TOKYO MEDICAL AND DENTAL UNIVERSITY, Tokyo (JP)

( * ) Notice: Subject to any disclaimer, the term of this patent is extended or adjusted under 35 U.S.C. 154(b) by 0 days.

(21) Appl. No.: 16/095,340

(22) PCT Filed: Apr. 21, 2017

(86) PCT No.: PCT/JP2017/016041
§ 371 (c)(1),
(2) Date: Oct. 19, 2018

(87) PCT Pub. No.: WO2017/183716
PCT Pub. Date: Oct. 26, 2017

(65) Prior Publication Data
US 2019/0128888 A1    May 2, 2019

(30) Foreign Application Priority Data
Apr. 21, 2016 (JP) ................................ 2016-085113

(51) Int. Cl.
*G01N 33/487* (2006.01)
*C12Q 1/04* (2006.01)
(Continued)

(52) U.S. Cl.
CPC ....... *G01N 33/48721* (2013.01); *C07K 17/08* (2013.01); *C07K 17/14* (2013.01);
(Continued)

(58) Field of Classification Search
None
See application file for complete search history.

(56) References Cited

U.S. PATENT DOCUMENTS 6,171,578 B1 *  1/2001  Dean ................. A61K 51/047
                                                424/1.11
2013/0256154 A1 * 10/2013  Peng ................. G01N 33/48721
                                                205/780.5

(Continued)

FOREIGN PATENT DOCUMENTS

JP    2013-090576 A    5/2013
JP    2014-210245 A    11/2014
(Continued)

OTHER PUBLICATIONS

Waseem A. et al., Lab on a Chip, vol. 12, pp. 2345-2352 (2012).
(Continued)

*Primary Examiner* — Melanie Brown
(74) *Attorney, Agent, or Firm* — McDermott Will & Emery LLP (57) ABSTRACT

A device for biological material detection includes a substrate; a through-hole through which a biological material to be tested passes, the through-hole being formed in the substrate; a molecule that interacts with the biological
(Continued)

material to be tested passing through, the molecule being formed in the through-hole; a first chamber member that forms, with at least the surface including the through-hole on one surface side of the substrate, a first chamber to be filled with electrolyte; and a second chamber member that forms, with at least the surface including the through-hole on the other surface side of the substrate, a second chamber to be filled with electrolyte. The biological material to be tested is identified by the waveform of the ion current (passage time, shape, etc.) when the biological material to be tested passes through the through-hole.

9 Claims, 8 Drawing Sheets

Specification includes a Sequence Listing.

(51) Int. Cl.
| | |
|---|---|
| C12M 1/34 | (2006.01) |
| C12Q 1/6825 | (2018.01) |
| C07K 17/14 | (2006.01) |
| G01N 15/12 | (2006.01) |
| C07K 17/08 | (2006.01) |
| G01N 33/483 | (2006.01) |
| C12M 1/00 | (2006.01) |
| C12Q 1/68 | (2018.01) |
| C12M 1/26 | (2006.01) |
| G01N 33/566 | (2006.01) |
| G01N 33/569 | (2006.01) |
| C07K 7/06 | (2006.01) |
| C07K 7/08 | (2006.01) |

(52) U.S. Cl.
CPC ............... *C12M 1/00* (2013.01); *C12M 1/34* (2013.01); *C12M 33/00* (2013.01); *C12Q 1/04* (2013.01); *C12Q 1/68* (2013.01); *C12Q 1/6825* (2013.01); *G01N 15/1218* (2013.01); *G01N 33/483* (2013.01); *G01N 33/566* (2013.01); *G01N 33/56983* (2013.01); *C07K 7/06* (2013.01); *C07K 7/08* (2013.01)

(56) References Cited

U.S. PATENT DOCUMENTS

| | | | | |
|---|---|---|---|---|
| 2014/0106472 | A1* | 4/2014 | Ervin | G01N 33/551 436/501 |
| 2014/0234366 | A1* | 8/2014 | Shimoide | A61K 36/00 424/195.15 |
| 2014/0374695 | A1* | 12/2014 | Astier | G01N 33/48721 257/9 |
| 2015/0204873 | A1* | 7/2015 | Ervin | G01N 33/92 435/7.4 |
| 2015/0377830 | A1* | 12/2015 | Baldauf | C12Q 1/6827 204/451 |
| 2016/0162634 | A1 | 6/2016 | Reid et al. | |
| 2016/0320286 | A1 | 11/2016 | Miki et al. | |
| 2018/0299424 | A1* | 10/2018 | Takulapalli | G01N 33/48721 |

FOREIGN PATENT DOCUMENTS

| | | |
|---|---|---|
| JP | 2014-531901 A | 12/2014 |
| JP | 2015-161521 A | 9/2015 |
| WO | 2013/137209 A1 | 9/2013 |

OTHER PUBLICATIONS

Chihiro Kawaguchi et al., "Electrical detection of single pollen allergen particles using electrode-embedded microchannels", Journal of Physics: Condensed Matter 24, 164202 (Mar. 30, 2012).

Akihide Arima et al., "Discrimination of equi-sized nanoparticles by surface charge state using low-aspect-ratio pore sensors", Applied Physics Letters 104, 163112 (2014).

Gaurav Goyal et al., "Low aspect ratio micropores for single-particle and single-cell analysis", Electrophoresis 36, 1164 (Apr. 20, 2015).

Krishnakumar et al., "Slowing DNA Translocation through a Nanopore Using a Functionalized Electrode", ACS Nano 7, 10319 (Oct. 28, 2013).

Samir M. Iqbal et al., "Solid-state nanopore channels with DNA selectivity", Nature Nanotechnology 2, 243 (Apr. 1, 2007).

Wei, R. et al., Stochastic sensing of proteins with receptor-modified solid-state nanopores, nature nanotechnology, Mar. 11, 2012, vol. 24, pp. 1-7.

English translation of International Preliminary Report on Patentability issued in corresponding International Patent Application No. PCT/JP2017/016041, dated Aug. 31, 2018.

Notice of Refusal issued in Japanese Patent Application No. 2018-513228, dated Sep. 2, 2019, with English translation.

* cited by examiner

DEVICE FOR BIOLOGICAL MATERIAL DETECTION, DETECTION APPARATUS FOR BIOLOGICAL MATERIAL DETECTION, METHOD FOR MEASURING ION CURRENT, AND METHOD FOR IDENTIFYING BIOLOGICAL MATERIAL

CROSS REFERENCE

This application is the U.S. National Phase under 35 U.S.C. § 371 of International Application No. PCT/JP2017/016041, filed on Apr. 21, 2017, which claims the benefit of Japanese application Ser. No., filed on 2016-085113, filed on Apr. 21, 2016, the entire contents of each are hereby incorporated by reference.

FIELD OF THE INVENTION

The present invention relates to a device for biological material detection (sometimes referred to simply hereinafter as the "device"), a detection apparatus for biological material detection (sometimes referred to simply hereinafter as the "detection apparatus"), a method for measuring an ion current (sometimes referred to simply hereinafter as the "measurement method"), and a method for identifying a biological material (sometimes referred to simply hereinafter as the "identification method"). In particular, the present invention relates to a device, detection apparatus, measurement method, and identification method that lengthen the time required for a sample such as a biological material to pass through a through-hole and make it possible to identify a sample by forming a molecule that interacts with the sample in the through-hole through which the sample passes.

DESCRIPTION OF THE RELATED ART

Devices that form a through-hole (nanopore) in a substrate and measure the ion current when a sample passes through the through-hole are drawing attention as devices capable of a wide range of applications in sensors for bacteria, viruses, DNA, proteins, and the like.

Figure 1:
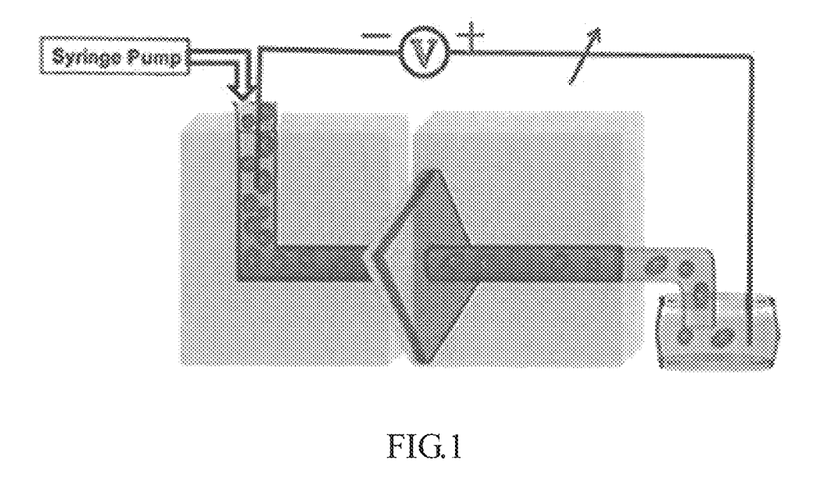
FIG. 1 is a drawing showing the prior art of a method for detecting the size and number of samples.

FIG. 1 shows the prior art of a method for detecting, inter alia, the sample size and quantity. The volume of the sample can be identified by detecting the changes in the ion current produced when the sample passes through pores (micropores) formed in a substrate such as silicon (see Non-patent Document 1). It is also known that an ion current that accords with the shape of a sample can be measured by making the thickness of the through-hole thinner than the sample (see Patent Document 1).

PRIOR ART DOCUMENTS

Patent Documents

[Patent Document 1] WO2013/137209

Non-Patent Documents

[Non-patent Document 1] Waseem A., et al. Lab on a Chip, Vol. 12, pp. 2345-2352 (2012)

SUMMARY OF THE INVENTION

Problems to be Solved by the Invention

The size and shape of a sample can be estimated from the changes in the ion current in the detection methods (devices) described in Patent Document 1 and Non-patent Document 1. The problem, however, is that it is difficult to identify the sample in the methods described in Patent Document 1 and Non-patent Document 1 when the sample size and shape are similar.

The present invention is intended to solve the above problems of the prior art. As a result of thoroughgoing research, it was discovered that (1) molecules that interact with a sample are formed in a through-hole through which the sample passes, whereby the sample passes through the through-hole while interacting with the molecule, (2) the time the sample takes to pass through the through-hole therefore lengthens and the waveform of the ion current measured changes when the sample that interacts with the molecule passes through the through-hole, and (3) as a result, the sample can be identified from the waveform of the ion current measured.

Specifically, the purpose of the present invention is to provide a device, a detection apparatus, a measurement method, and an identification method by which molecules that interact with a sample are formed in a through-hole.

Means Used to Solve the Abovementioned Problems

The present invention, which is shown below, relates to a device, a detection apparatus, a measurement method, and an identification method.

(1) A device for biological material detection comprising
a substrate,
a through-hole through which a biological material to be tested passes, the through-hole being formed in the substrate,
a molecule that interacts with the biological material to be tested passing through, the molecule being formed in the through-hole,
a first chamber member that forms, with at least the surface including the through-hole on one surface side of the substrate, a first chamber to be filled with electrolyte and
a second chamber member that forms, with at least the surface including the through-hole on the other surface side of the substrate, a second chamber to be filled with electrolyte,
the biological material to be tested being identified by the waveform of the ion current when the biological material to be tested passes through the through-hole.

(2) The device for biological material detection according to (1) above,
wherein the biological material to be tested is one or more of bacteria, viruses, DNA, and proteins.

(3) The device for biological material detection according to (1) or (2) above,
wherein the interacting molecule is a peptide, a sugar chain, or a nucleic acid.

(4) The device for biological material detection according to any of (1)-(3) above,
wherein the interacting molecule is a flagellin-recognizing peptide of SEQ ID NO: 2.

(5) The device for biological material detection according to any of (1)-(3) above,
wherein the interacting molecule is an influenza-recognizing peptide selected from SEQ ID NOS: 3 to 5.

(6) The device for biological material detection according to any of (1)-(3) above,
wherein the interacting molecule includes an influenza-recognizing sugar chain (6'-sialyllactose).

(7) The device for biological material detection according to any of (1)-(3) above,
wherein a metal layer is laminated in the through-hole and the interacting molecule is formed on the metal layer.

(8) A detection apparatus for biological material detection including,
the device for biological material detection according to claim 1,
a first electrode formed in the first chamber,
a second electrode formed in the second chamber, and
an ammeter for measuring the ion current when a sample passes through the through-hole.

(9) A method for measuring an ion current in which a measurement is made of the ion current when a biological material to be tested passes through a through-hole formed in a substrate,
wherein a molecule that interacts with the biological material to be tested is formed in the through-hole, and the biological material to be tested passes through the through-hole while interacting with the molecule, whereby the biological material to be tested is identified by differences in the waveform of the ion current.

(10) The method for measuring an ion current according to (9) above,
wherein the biological material to be tested is one or more of bacteria, viruses, DNA, and proteins.

(11) The method for measuring an ion current according to (9) or (10) above,
wherein the interacting molecule is a peptide, a sugar chain, or a nucleic acid.

(12) The method for measuring an ion current according to any of (9)-(11) above,
wherein the interacting molecule is a flagellin-recognizing peptide of SEQ ID NO: 2.

(13) The method for measuring an ion current according to any of (9)-(11) above,
wherein the interacting molecule is an influenza-recognizing peptide selected from SEQ ID NOS: 3 to 5.

(14) The method for measuring an ion current according to any of (9)-(11),
wherein the interacting molecule includes an influenza-recognizing sugar chain (6'-sialyllactose).

(15) A method for identifying a biological material that identifies a biological material to be tested from the ion current measured by the method for measuring an ion current according to (9)-(14) above.

Advantages of the Invention

When the device of the present invention is used, the time the sample takes to pass through the through-hole increases when a sample that interacts with the molecule passes through the through-hole. Samples of similar size can therefore be identified by analyzing the waveform of the ion current measured.

BRIEF DESCRIPTION OF THE DRAWINGS

FIG. 11 is graphs in which waveforms of ion currents measured in Example 8 using a molecule of SEQ ID NO: 3 in FIG. 11(A), a molecule of SEQ ID NO: 4 in FIG. 11(B), and a molecule of SEQ ID NO: 5 in FIG. 11(C) are superimposed.
FIG. 11(D) is a graph in which waveforms of ion currents measured in Comparative Example 7 are superimposed.

DESCRIPTION OF THE PREFERRED EMBODIMENTS

The device, detection apparatus, measurement method, and identification method are described in detail below.

Figure 2:
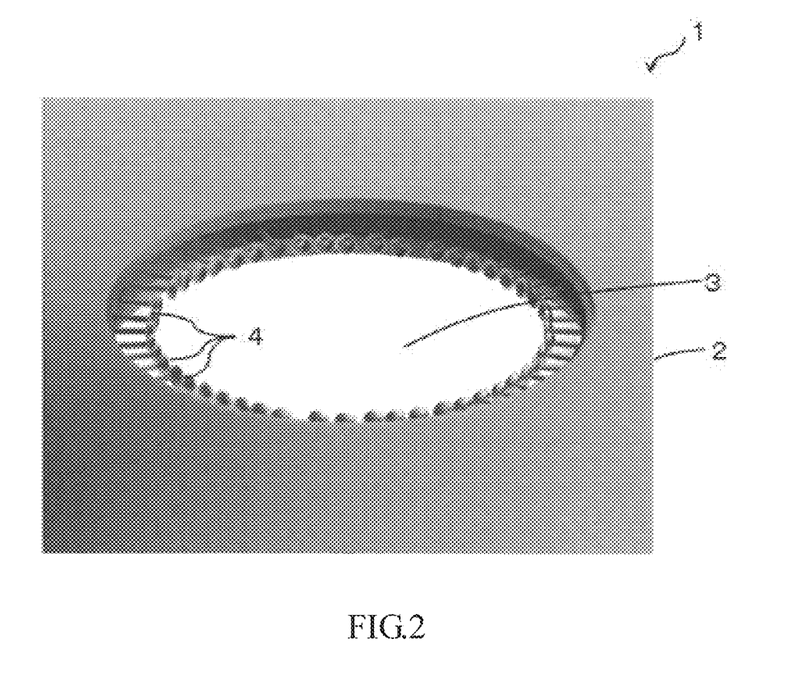
FIG. 2 is a drawing showing an outline of a device 1 of the present invention.

FIG. 2 shows an outline of a device 1 of the present invention. The device 1 of the present invention includes at least a substrate 2, a through-hole 3 formed in the substrate 2 through which the sample passes, and a molecule that interacts with the sample (sometimes referred to simply hereinafter as the "molecule") 4 formed in the through-hole 3.

The device 1 shown in FIG. 2 can also be incorporated as a detection device of a detection apparatus using a known through-hole.

There are no particular limitations to the substrate 2 as long as an insulating material commonly used in the field of semiconductor manufacturing technology is used therefor. Examples include Si, Ge, Se, Te, GaAs, GaP, GaN, InSb, InP, and SiNx. Also, the substrate 2 may be formed in the shape of a thin film called a solid membrane using a material such as SiNx, $SiO_2$, or $HfO_2$ or in the shape of a sheet called a two-dimensional material using a material such as graphene, graphene oxide, molybdenum dioxide ($MoS_2$) [sic], or boron nitride (BN). The substrate 2 in which through-hole 3 is formed is preferably thin since the sample detection sensitivity becomes higher as the volume of the through-hole 3 becomes smaller. For example, the substrate 2 is preferably 5 μm or less, more preferably 500 nm or less, even more preferably 100 nm or less, and ideally 50 nm or less. Furthermore, graphene, for example, can yield a substrate 2 that is 1 nm or less in thickness, and the film can be made extremely thin when a solid membrane or a two-dimensional material is used as the substrate 2. However, the substrate 2 sometimes becomes difficult to handle without damage at extremely small thicknesses. The substrate 2, therefore, may be a laminated structure in which a solid membrane or two-dimensional material is laminated on top of a support plate formed of the above insulating materials.

When making a laminated structure, a solid membrane or a two-dimensional material is laminated on top of a support plate in which a hole larger than the through-hole 3 has been formed, and a through-hole 3 may be formed in solid membrane or two-dimensional material.

The through-hole 3 is formed to penetrate the substrate 2. The smaller the volume of the through-hole 3 when detecting an ion current, the higher the sensitivity. Therefore, together with thinning the substrate 2 as described above, the size of the through-hole 3 may be adjusted appropriately so that it is larger than the sample to be measured, but not excessively so. Examples of the sample include bacteria, cells, viruses, DNA, RNA, proteins, pollen, and other such biological materials. However, there are no particular limitations as regards the sample as long as the sample interacts with the molecule 4. Examples include non-biological materials such as sulfur oxides ($SO_x$), nitrogen oxides ($NO_x$), volatile organic compounds (VOC), and mineral oxides (such as silicon, aluminum, titanium, and iron).

However, there are no particular limitations as regards the molecule 4 as long as the molecule 4 reacts with the sample. Furthermore, "interaction" in the present invention means that a weak binding force is at work between the molecule 4 and the sample to be measured by the molecule 4 recognizing the sample to be measured or exerting an effect on the sample to be measured, and the molecule lengthens the time the sample to be measured takes to pass through the through-hole 3 in comparison to when the molecule 4 is not formed in the through-hole 3. Examples of interactions include ionic interaction, hydrogen bonding, and electrical interaction. Therefore, molecules that bond firmly with the sample to be measured and do not separate are not included in molecule 4 of the present invention.

Examples of the molecule 4 include peptides, nucleic acids, sugar chains, and organic molecules. For the molecule 4, peptides, nucleic acid sequences, surface molecules, and the like specific to the sample to be measured are studied and a peptide or nucleic acid sequence, or a sugar chain or the like that bonds weakly with the specific peptide, nucleic acid, surface molecule or the like may be determined. In the case of a peptide, for example, as a weak binding sequence, examples include a partial sequence of an antibody sequence that recognizes the specific peptide of the sample to be measured or a sequence that interacts with a surface molecule of the sample to be measured. Also, when the weak binding sequence is a nucleic acid, examples include part of a sequence that hybridizes with a specific nucleic acid of the sample to be measured. Both peptides and nucleic acids may be synthesized by known peptide synthesis apparatus and nucleic acid synthesis apparatus if the sequence is determined. In addition, a contracted peptide and nucleic acid synthesis service may be utilized. Also, when the weakly binding molecule is a sugar chain, a sugar chain that interacts with a specific peptide or surface molecule of the sample to be measured may be selected. When the sample to be measured is a non-biological material, surface charge and the like, for example, are studied, and an organic molecule having a charge that interacts with the charge may be selected.

Furthermore, the molecules 4 given as examples above are examples of when the sample one wishes to measure is decided in advance, but samples that interact with the nucleic acid can also be screened by forming arbitrarily designed nucleic acids, peptides, sugar chains, and the like in the through-hole. For example, one could assume a case in which bacteria, viruses, and the like that may bond with a protein or sugar chain on a human cell surface are screened. In this case, a desired protein or sugar chain from the human cell surface is selected, and a peptide or sugar chain is designed based on the protein or sugar chain. Also, a device in which the designed peptide or sugar chain is formed in the through-hole and a device in which the designed peptide or sugar chain is not formed are produced, and samples having different waveforms of the ion current may be selected when the sample flows. In other words, the "molecule that interacts with the sample" may be one where the fact that the molecule interacts with a specific sample is clear in advance, or one where the sample with which the molecule interacts is not known (there is a possibility of interaction). As described above, the molecule 4 formed in the through-hole 3 may be nucleic acid, peptide, sugar, chain, organic molecule, etc., designed as desired.

There are no particular limitations as to the molecule 4 provided that the molecule 4 can be formed in the through-hole 3. For example, a metal layer may be formed by vapor depositing a metal such as gold, platina, aluminum, copper, iron, cobalt, silver, lead, indium, zinc, gallium, chromium, or titanium in the through-hole 3, and the molecule 4 may be formed on the metal layer by immersing the substrate 2 in an aqueous solution containing the molecule 4. When the molecule 4 is a peptide, a sequence may be designed so that one end of the peptide contains a thiol group, and the thiol group and metal layer may be adsorbed. In addition, when the molecule 4 is a nucleic acid, a thiol group may be introduced into the nucleic acid by a known method and adsorbed to the metal layer. Also, when the molecule 4 is a sugar chain, part of the sugar chain may be substituted by a thiol group by a known method.

Figure 3:
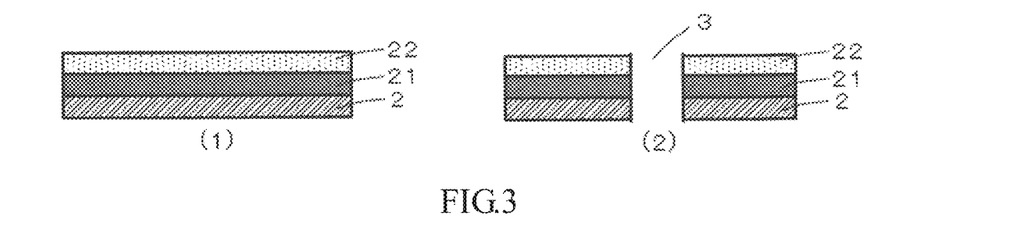
FIG. 3 is a drawing for explaining a method for forming a metal layer in a through-hole 3.
Figure 4:
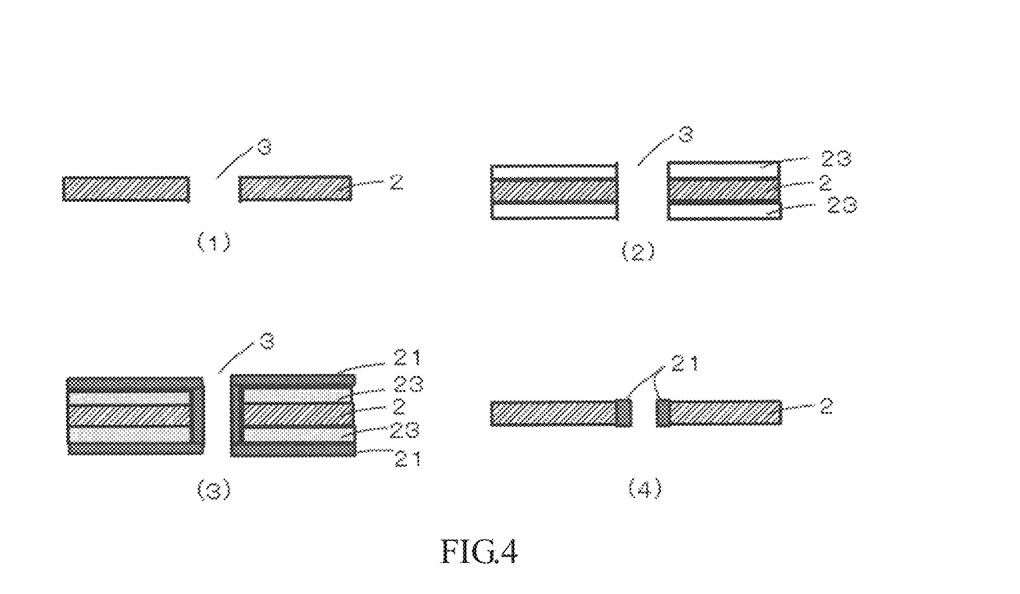
FIG. 4 is a drawing for explaining a method for forming a metal layer in a through-hole 3.

FIGS. 3 and 4 illustrate a method for forming a metal layer in a through-hole 3. In the example shown in FIG. 3, (1) a metal layer 21 is first laminated by sputtering, etc., on top of the substrate 2, and an insulating layer 22 is then laminated by sputtering, etc., on top of the metal layer 21. Examples of the insulating layer 22 include $SiO_2$, $SiN_x$, SiON, $Al_2O_3$, $Y_2O_3$, $Ta_2O_5$, and $HfO_2$, but there is no particular limitation as long as the insulating layer 22 is an insulating material. (2) Then, the part that forms the through-hole 3 is drawn by electron beam drawing, and the through-hole 3 is formed by reactive ion etching or the like. The metal layer 21 in the through-hole 3 can be exposed by the above method.

In the sample shown in FIG. 4, (1) a through-hole 3 is first formed in the substrate 2. The through-hole 3 may be drawn in the same way as above by electron beam drawing and formed by reactive ion etching or the like. (2) An electron beam resist 23 is applied to the substrate 2, and the periphery of the through-hole 3 is covered by the electron beam resist 23 by electron beam drawing. The electron beam resist 23 may be either a negative or positive type. (3) A metal layer 21 is laminated on the through-hole 3 and electron beam resist 23 by sputtering or the like. (4) The metal layer 21 on the electron beam resist is also removed by lifting off the electron beam resist 23, and a metal layer 21 can be formed in the through-hole 3.

Furthermore, a thiol group of the molecule 4 is adsorbed onto the metal layer 21 in the examples shown in FIGS. 3 and 4, but a metal layer 21 need not be provided as long as the molecule 4 can be formed in the through-hole 3. For example, when $SiO_2$ is used as the material of the substrate 2, the molecule 4 may be bonded to the substrate 2 by introducing an amino group or carboxyl group into the molecule 4 through a silane coupling reaction. Also, the through-hole 3 part of the substrate 2 may be covered by polyurethane, and a molecule 4 having modified polydopamine as a scaffold may be bonded to the polyurethane surface.

Figure 5:
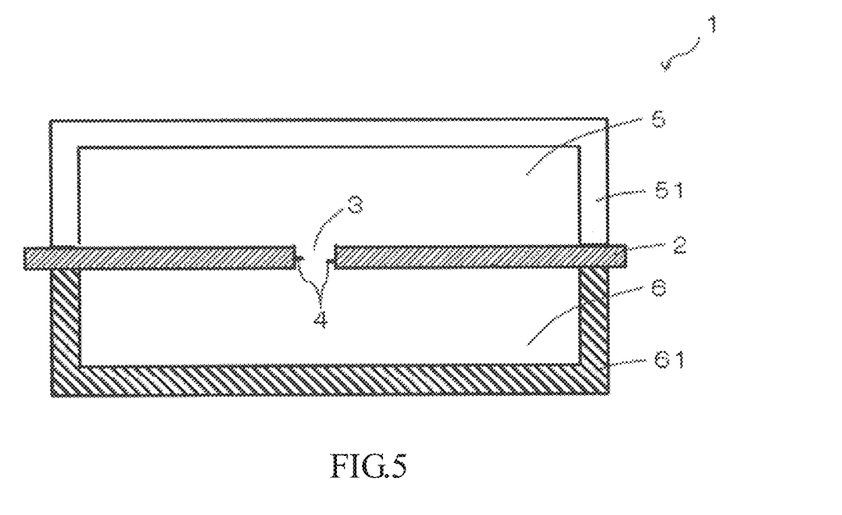
FIG. 5 is a drawing showing another embodiment of a device 1.

FIG. 5 shows another embodiment of the device 1. The device 1 shown in FIG. 5 includes at least a first chamber member 51 capable of forming a first chamber 5 to be filled with electrolyte with a surface containing at least the through-hole 3 on one side of the substrate 2 and a second chamber member 61 capable of forming a second chamber 6 to be filled with electrolyte with a surface containing at least the through-hole 3 on the other side of the substrate 2.

The first chamber member 51 and the second chamber member 61 are preferably formed of an electrically and chemically inert material. Examples include glass, sapphire, ceramic, resin, rubber, elastomer, $SiO_2$, SiNx, and $Al_2O_3$.

The first chamber 5 and the second chamber 6 are formed to hold the through-hole 3 therebetween and no limitation is provided thereby as long as the first chamber 5 and the second chamber 6 are formed so that a sample introduced into the first chamber 5 can move through the though-hole 3 into the second chamber 6. For example, a first chamber member 51 and a second chamber member 61 may be produced separately and adhered to be liquid-tight to the substrate 2. Alternatively, a box member that is approximately cuboid in shape having one side open may be formed, the substrate 2 may be inserted and fixed in the center of the box, and the open side may be sealed liquid-tight. This case means that the first chamber 51 and the second chamber 61 are not separate members and means that the box member is separated with the substrate 2 as the boundary. Furthermore, although not shown in the drawing, holes for filling and discharging electrolyte and sample solution and inserting electrodes and/or leads may be formed as needed in the first chamber member 51 and the second chamber member 61.

Figure 6:
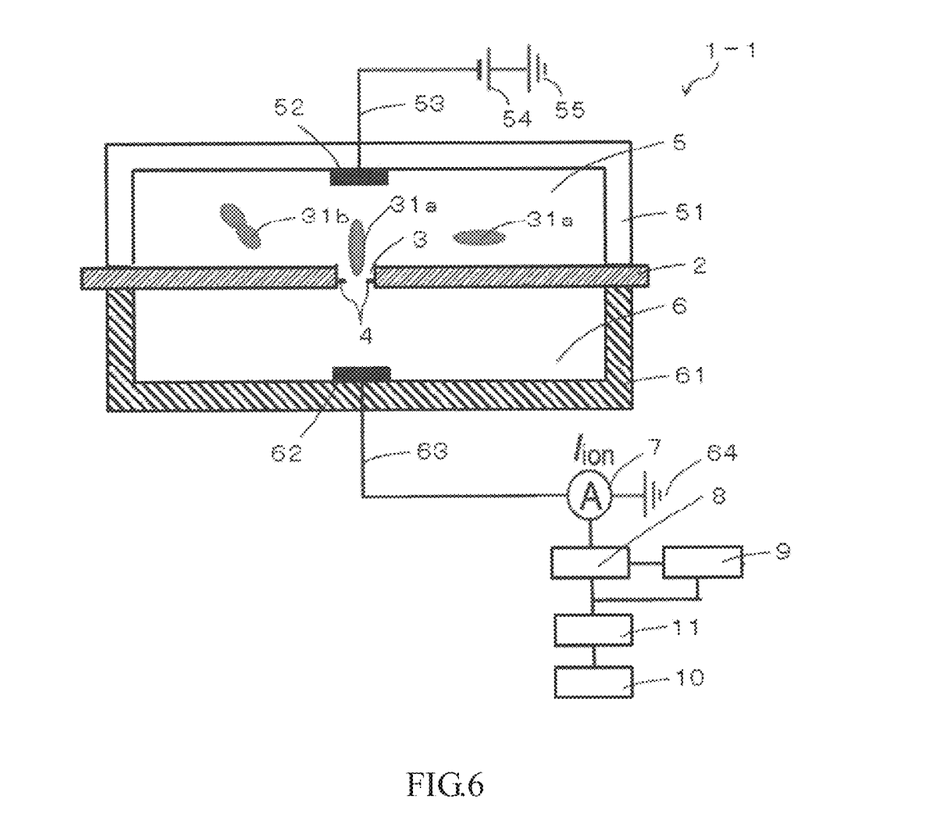
FIG. 6 is a schematic drawing showing an example of a detection apparatus of the present invention.

FIG. 6 is a schematic drawing showing an example of the detection apparatus 1-1 of the present invention. The detection apparatus 1-1 includes, in addition to the device 1, at least a first electrode 52 formed at a location in contact with the electrolyte inside the first chamber 5, a second electrode 62 formed at a location in contact with the electrolyte inside the second chamber 6, and an ammeter 7 for measuring the ion current when samples 31a, 31b pass through the through-hole 3.

Also, the detection apparatus 1-1 may include an analysis unit 8 for analyzing the ion current measured by the ammeter 7, a display unit 9 for displaying the measured ion current values and/or the results analyzed by analysis unit 8, program memory 10 which stores in advance programs to make the analysis unit 8 and the display unit 9 function, and a control unit 11 for reading and executing the programs stored in the program memory 10 as needed. The programs may be recorded in the program memory 10 in advance or may be recorded on a recording medium and stored in the program memory 10 using an install means.

The first electrode 52 and the second electrode 62 can be formed of a known conductive metal such as aluminum, copper, platinum, gold, silver, or titanium. The first electrode 52 and the second electrode 62 are formed so that the through-hole 3 is between them and transport ions in the electrolyte when a direct current is applied. Therefore, the first electrode 52 may be formed at a place in contact with the electrolyte inside the first chamber 5 and may be disposed on the surface of the substrate 2, on an inside surface of the first chamber member 51, or in the space inside the first chamber 5 via a lead 53. The second electrode 62 as well, like the first electrode 51, may be formed at a place in contact with the electrolyte inside the second chamber 6 and may be disposed on the surface of the substrate 2, on an inside surface of the second chamber member 61, or in the space inside the second chamber 6 via a lead 63. Furthermore, in the example shown in FIG. 5, the first electrode 52 is formed on an inside surface of the first chamber member 51 and the second electrode 62 is formed on an inside surface of the second chamber member 6. The first electrode 52 and the second electrode 62 may be inserted from holes formed in the first chamber member 51 and the second chamber member 61.

The first electrode 52 connects to a power source 54 and a ground 55 via a lead 53. The second electrode 62 connects to the ammeter 7 and a ground 64 via a lead 63. Furthermore, in the example shown in FIG. 6, the power source 54 connects to the first electrode 52 side and the ammeter 7 connects to the second electrode 62 side, but the power source 54 and ammeter 7 may be provided on the same electrode side.

There are no particular limitations as regards the power source 54 the power source 54 can conduct a direct current to the first electrode 52 and the second electrode 62. There are no particular limitations as regards the ammeter 7 as long as the ammeter 7 can measure the ion current generated when power is applied to the first electrode 52 and the second electrode 62 over time. Furthermore, although not shown in FIG. 6, a noise removal circuit, voltage stabilization circuit, and the like may be provided as needed.

When a sample passes through the through-hole 3 in the detection apparatus 1-1 of the present invention, the ion current flowing through the through-hole is blocked by the sample, and the ion current decreases. This decrease in the ion current is proportionate to the volume of the sample in the through-hole 3. However, in a conventional detection apparatus, if the sample volumes are essentially the same, it has been difficult to identify from the measured values of the ion current if the samples were of the same type or different types. In the present invention, even if the sample volume is the same, a sample that interacts with the molecule 4 and a sample that does not interact with the molecule 4 have a clearly different passage time through the through-hole 3. Therefore, the type of sample can be identified by analyzing the ion current change time (time from the sample entering to exiting the through-hole 3) and waveforms.

Also, even if of the same type, there are samples of different shapes such as exosomes and DNA base sequences. With samples 31a and 31b shown in FIG. 6, since the volume changes inside the through-hole 3 differ during passage through the through-hole 3, the waveform of the ion current measured differs. However, in a conventional detection apparatus 1-1, it was difficult to measure differences in the shape of the sample accurately because the speed of passage of the sample through the through-hole 3 was rapid. In the present invention, since interaction with the molecule 4 lengthens the time it takes the sample to pass through the through-hole 3, differences in the shape of samples of the same type can also be expected to be measured.

The analysis unit 8 analyzes the values (waveforms) of the ion current measured by the ammeter 7. When the sample is not spherical, even samples of the same type as shown in FIG. 6 may have different waveforms (passage time, shape, etc.) of the ion current measured when the orientation differs when entering the through-hole 3. In such cases, analysis may be performed based on a data assembly.

The display unit 9 may be a known display unit such as a liquid-crystal display, plasma display, organic EL device, or the like as long as display unit 9 can display the values (waveforms) of the ion current measured and the results analyzed by the analysis unit 8.

Next, the measurement method and identification method using the detection apparatus 1-1 of the present invention will be explained. The measurement method can be carried out by the following procedure.

(1) The first chamber 5 and the second chamber 6 are filled with electrolyte. There are no particular limitations as to the electrolyte as long as the electrolyte can energize the first electrode 52 and the second electrode 62; TE buffer, PBS buffer, HEPES buffer, KCl aqueous solution, and the like may be used. A liquid junction then forms between the inside of the first chamber 5 and the inside of the second chamber 6 via the through-hole 3.

(2) The sample is added to the first chamber 5.

(3) The first electrode 52 and the second electrode 62 are energized by the power source 54. The values of the ion current generated by this energization are measured over time by the ammeter 7. Furthermore, samples such as bacteria have surface charge [sic; surface charge]. Therefore, when the first electrode 52 and the second electrode 62 are energized, in addition to normal diffusion, the sample added to the first chamber 5 passes through the through-hole 3 formed in the substrate 2 by electrophoresis and moves to the second chamber 6. However, pressure may be applied as needed by a pump or the like to a solution in which a sample is dispersed so that the sample passes through the through-hole 3 by water flow.

The ion current when the sample passes through the through-hole 3 of the detection apparatus 1-1 can be measured by the above procedure. The sample identification method may then identify the sample from the results measured by the ion current measurement method. Specifically, the sample size is understood from the degree of lowering of the ion current measured value. Also, even when the sample size is the same, the type of sample can be specified from the time from when the ion current measured value changes and returns to a constant state and the waveforms since one can understand whether the sample interacts with the molecule 4.

Examples are given below to explain the present invention in further detail. The examples, however, are merely provided as a reference to concrete embodiments to explain the present invention. These examples are to explain specific concrete embodiments of the present invention but are not given to limit or restrict the scope of the invention disclosed in the present application.

EXAMPLES

[Production of Device 1]

Example 1

First, a silicon wafer (E&M Co., Ltd.) with a (100) plane orientation having a 50 nm silicon nitride film on both surfaces was cut to 29 mm square. One surface of the substrate was covered with a metal mask to prevent etching in which holes had been formed in an area of about 500 μm square. The silicon nitride film was removed from only the 500 μm square area in which the holes were formed by an RIE apparatus (RIE-10NR, Samco Co., Ltd.), and the silicon surface was exposed. Only the silicon of the exposed part was selectively wet etched thereafter on a 125° C. hot plate (hot plate Ninos ND-1, As One Co., Ltd.) over about three hours by potassium hydroxide aqueous solution (Wako Pure Chemicals Co., Ltd.). The silicon was etched until reaching the silicon nitride film on the other surface of the substrate by this operation. The hole in the silicon that reached the silicon nitride film was about 150 μm square.

Next, a pattern of a through-hole 3 was drawn by electron beam drawing substantially in the center of the silicon nitride film covering the above silicon hole of about 150 μm square. Then, development was performed by immersion in developing solution, and a cylindrical through-hole 3 about 2 μm in diameter was formed in the silicon nitride film by reactive ion etching by an RIE apparatus.

Figure 7:
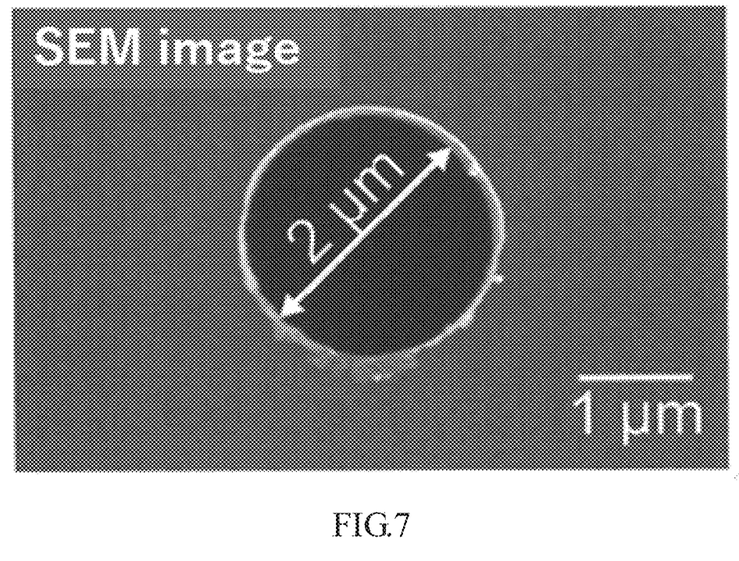
FIG. 7 is a photograph substituted for a drawing and is an SEM image of near a through-hole 3.

Next, the silicon nitride was coated by an electron beam resist (ZEP520A, manufactured by Nippon Zeon Co., Ltd.) using a spin coater (MS-B100, manufactured by Mikasa Co., Ltd.). After baking at 180° C. on the hot plate, the resist surrounding the through-hole 3 was removed by electron beam drawing. Next, gold was vapor deposited in the through-hole 3 using an SVC-700LRF manufactured by Sanyu Electronics Co., Ltd. FIG. 7 is an SEM image of near through-hole 3. Vapor deposition of gold around through-hole 3 from which the electron beam resist had been removed was confirmed. Although it is difficult to understand from the photograph, gold was also confirmed to be vapor deposited on the inner surface of through-hole 3.

Next, a peptide that interacts with *Escherichia coli* was formed in the through-hole 3 by the following procedure.

(1) A peptide that interacts with a sugar chain on the *E. coli* surface was designed. The amino acid sequence of the peptide designed is shown below.

G R H I F W R R G G G C (SEQ ID NO: 1)

(2) A peptide of the designed amino acid sequence was synthesized by a conventional method, diluted to 1 mM in phosphate-buffered physiological saline (PBS), and a peptide solution was produced.

(3) The peptide solution produced in (2) above was applied dropwise to the through-hole 3 of the device 1 and allowed to stand for two hours at room temperature.

(4) The peptide solution was rinsed several times by PBS. A device 1 was produced by the above procedure.

[Production of Detection Apparatus 1-1]

Example 2

Next, polymer blocks (manufactured by Toray Co., Ltd.) of polydimethylsiloxane (PDMS) provided with holes for introduction of electrodes, electrolyte, and sample were affixed in a liquid-tight manner above and below the substrate 2 of the device 1 produced in Example 1, and a first chamber 5 and a second chamber 6 were produced. The capacity of the first chamber 5 and second chamber 6 was about 10 μL each. Using silver-silver chloride electrodes for the first electrode 52 and the second electrode 62, electrode were inserted into the first chamber 5 and the second chamber 6 from the holes provided in the polymer blocks. A battery-powered bias power source (Axisnet) was used as the power source 54 and connected to the first electrode 52 via a lead. Data were acquired using a digitizer having a current amplifier and high time resolution of 1 MHz (NI5922, National Instruments) as ammeter 7, and the acquired data were stored on a RAID drive HDD (HDD-8263, National Instruments Co.).

Comparative Example 1

A detection apparatus was produced by the same procedure as in Example 2 except that gold vapor deposition and peptide bonding were not performed on the device produced in Example 1.

[Measurement of Ion Current and Identification]

Next, the ion current when the sample passed through the through-hole 3 was measured using the detection apparatus 1-1 produced. Sample preparation and the measurement method were as follows.

(1) Sample Preparation

*E. coli* (JM109; Takara Bio Co., Ltd.) and *Bacillus subtilis* (25975; ATCC) were used in the samples. The size of *B. subtilis* was 0.7-0.8×3.0 µm, and the size of *E. coli* was 0.5×1.0-3.0 µm; they were of substantially the same size. A sample was cultured by a conventional method. The culture broth was precipitated by centrifugation, the precipitate was washed by 2.5% LB medium (LB Broth Miller, Sigma-Aldrich Co., LLC.), then precipitated by centrifuging again. The precipitate was diluted to $5\times10^7$ cells/mL by phosphate-buffered physiological saline (PBS) to prepare an *E. coli* suspension.

(2) Measurement of Ion Current

The second chamber 6 of the detection apparatus 1-1 produced in Example 2 and Comparative Example 1 was filled with electrolyte (PBS buffer, manufactured by Wako Pure Chemicals Co., Ltd.). Next, 10 µL of the sample prepared in (1) above diluted 100-fold by PBS buffer was added to the first chamber 5, a voltage of 50 mV was applied to the first electrode 52 and the second electrode 62, and the ion current $I_{ion}$ was measured.

Example 3

Using *E. coli* as the sample, the ion current was measured using the detection apparatus 1-1 produced in Example 2.

Comparative Example 2

The ion current was measured in the same way as in Example 3 except that the detection apparatus 1-1 produced in Comparative Example 1 was used instead of the detection apparatus 1-1 produced in Example 2.

Figure 8:
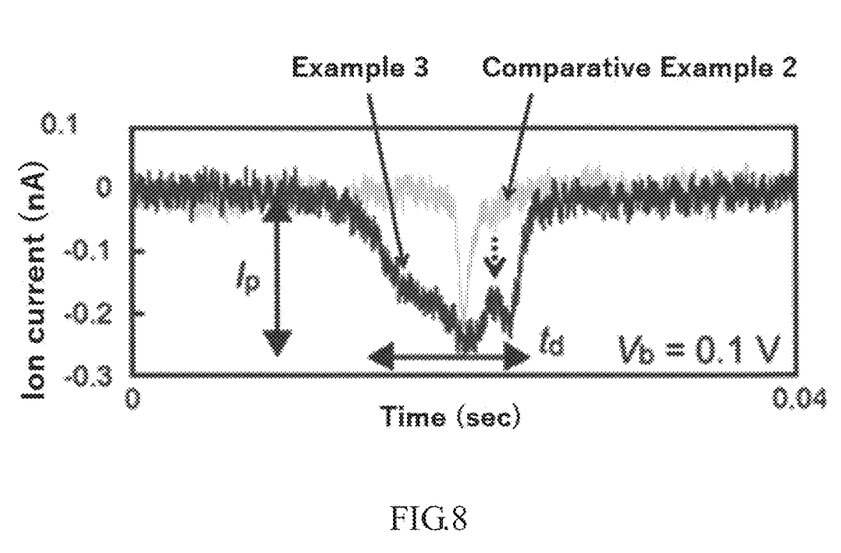
FIG. 8 is a graph in which waveforms of ion currents measured in Example 3 and Comparative Example 2 are superimposed.

FIG. 8 is a graph in which waveforms of ion currents of one sample each measured in Example 3 and Comparative Example 2 are superimposed. As is evident from FIG. 8, the *E. coli* size could be measured correctly in the measurements of Example 3 and Comparative Example 2 since the lowered ion current value (Ip) was the same in both Example 3 and Comparative Example 2. On the other hand, the time (td) from when the ion current value was lowered by entry of the sample into the through-hole 3 until the ion current value returned to a steady state by the sample exiting the through-hole 3 was clearly longer in Example 3 than in Comparative Example 2. Also, lengthening the time it takes the sample to pass through the through-hole 3 made visible waveforms that could not be observed in conventional measurement, as shown by the dotted-line arrow in the drawing. Since the lowering of the ion current value is proportionate to the amount of sample in the through-hole 3, the measurement method of the present invention is thought to have more correctly measured the shape of the sample.

Example 4

Figure 9:
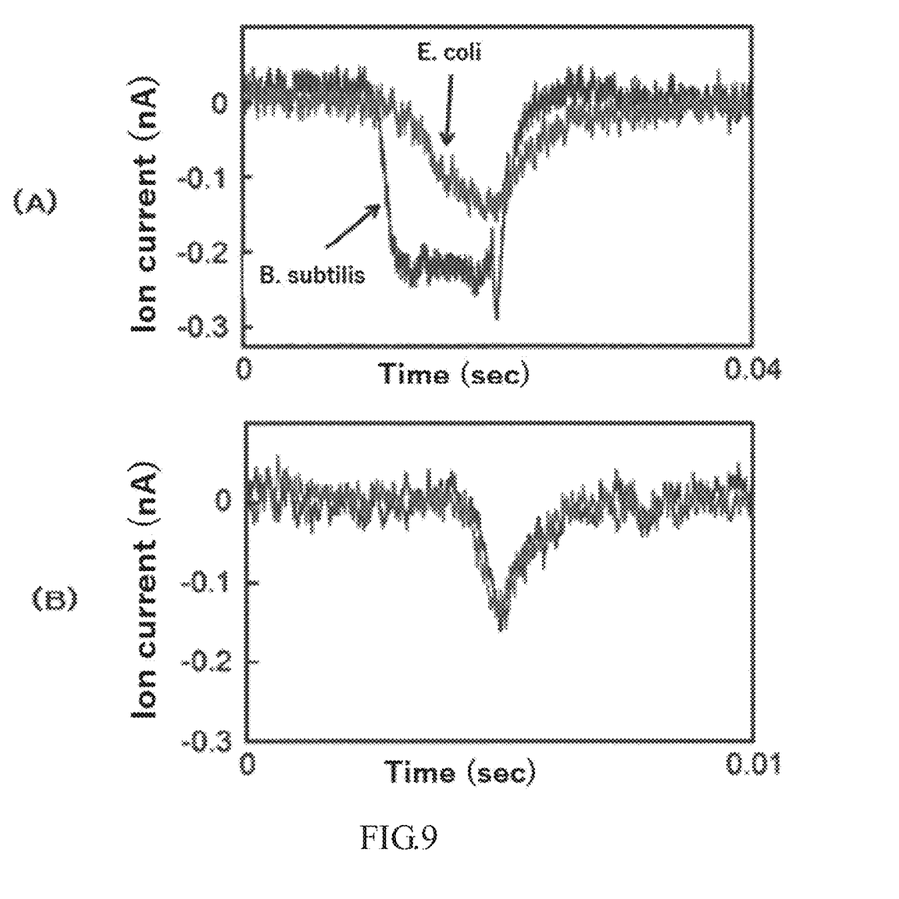
FIG. 9(A) is a graph in which waveforms of ion currents measured in Example 4 are superimposed.
FIG. 9(B) is a graph in which waveforms of ion currents measured in Comparative Example 3 are superimposed.

The ion currents of *E. coli* and *B. subtilis* were measured by the same procedure as in Example 3 except that the diameter of the through-hole 3 was set at about 3 µm. FIG. 9(A) is a graph of the results measured in Example 4.

Comparative Example 3

The ion currents of *E. coli* and *B. subtilis* were measured by the same procedure as in Example 3 except that the diameter of the through-hole 3 was set at about 3 µm. FIG. 9(B) is a graph of the results measured in Comparative Example 3.

As shown in FIG. 9(B), the ion current waveforms measured for *E. coli* and *B. subtilis* were basically the same when a detection apparatus without a molecule formed in through-hole 3 was used, and the two could not be distinguished. As shown in FIG. 9(A), the ion current waveforms measured for *E. coli* and *B. subtilis* clearly differed due to interaction with the molecule when a detection apparatus having a molecule formed in the through-hole 3 was used. The above results clarified that forming a molecule that interacts with the sample in the through-hole 3 makes it possible to identify the sample, even when samples are of basically the same size.

Next, various experiments were conducted that varied the type of interacting molecule and type of sample.

[Identification of Flagellated *E. coli* and Non-Flagellated *E. coli*, Molecule: Peptide]

Example 5

A device 1 was produced by the same procedure as in Example 1 except that the diameter of the through-hole 3 was set at about 300 nm and a peptide designed to interact with the flagella of *E. coli* was used as the molecule 4, and a detection apparatus 1-1 was then produced by the same procedure as in Example 2. The amino acid sequence of the designed peptide appears below.

(SEQ ID NO: 2)
FLLRVPHLGGGC

Comparative Example 4

A device and detection apparatus were produced by the same procedures as in Example 5 except that the peptide shown by SEQ ID NO: 2 was not formed in the through-hole.

Examples 6 (with Molecule) and Comparative Example 5 (without Molecule)

Next, samples were prepared by the same procedure as in [Measurement of ion current and identification] above except that the detection apparatus produced in Example 5 and Comparative Example 4 were used and *E. coli* having flagella [*Escherichia coli*, BW25113 (National Bio Resource Project, Keio Collection)] and *E. coli* without flagella due to a lack of FliC, the main protein that constructs the flagella [*Escherichia coli*, ΔfliC (National Bio Resource Project, Keio Collection)] were used as the samples, and the ion current was measured. Furthermore, the size of the *E. coli* was basically the same, except for the presence or absence of flagella.

Figure 10:
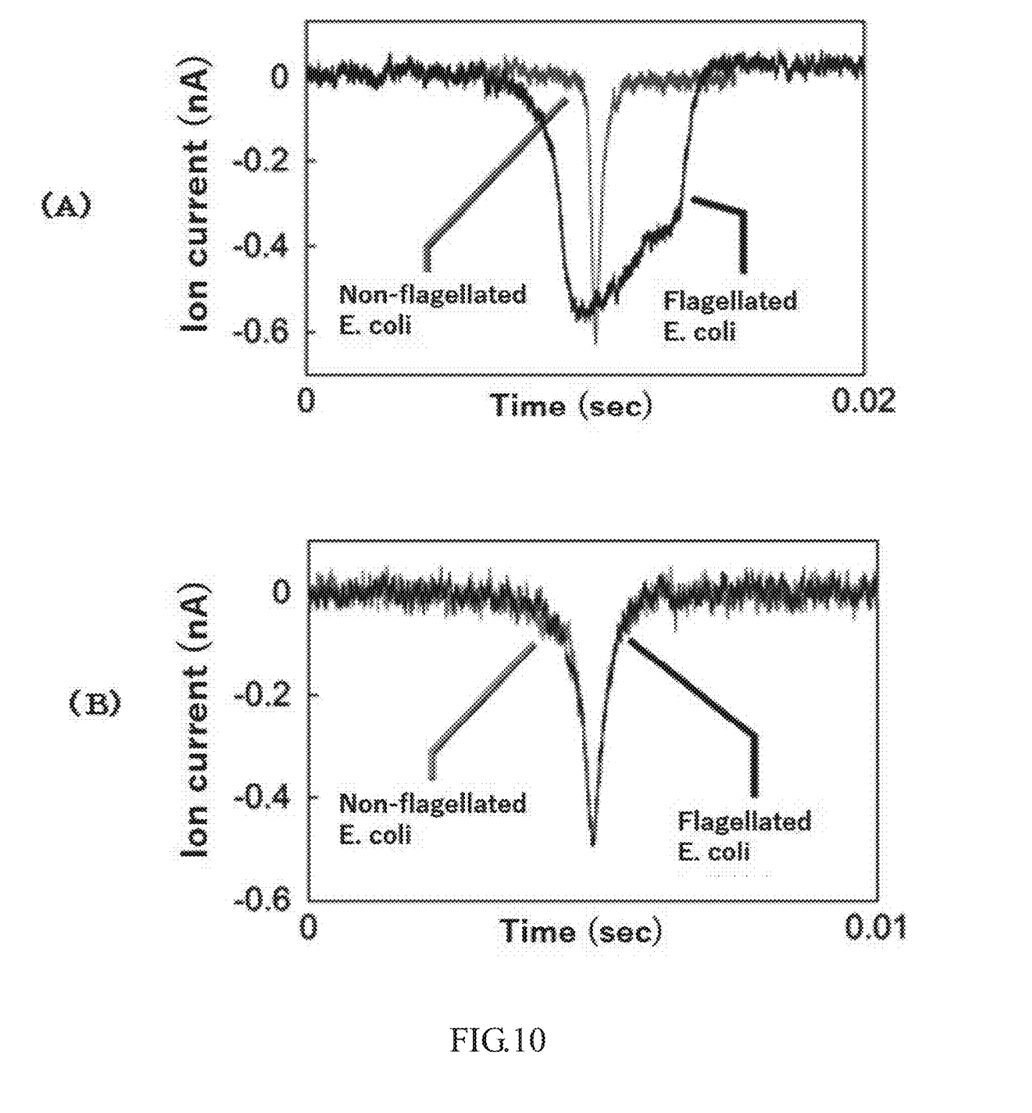
FIG. 10(A) is a graph in which waveforms of ion currents measured in Example 6 are superimposed.
FIG. 10(B) is a graph in which waveforms of ion currents measured in Comparative Example 5 are superimposed.

FIG. 10(A) is a graph in which waveforms of ion currents of one sample each measured in Example 6 are superimposed. As is evident from FIG. 10(A), when the ion current value (Ip) was measured by the detection apparatus of Example 5 in which a peptide that recognizes the flagella of *E. coli* was bonded to the through-hole, the ion current value waveforms clearly differed depending on the presence or absence of flagella. FIG. 10(B) is a graph in which the waveforms of ion currents of one sample each measured in Comparative Example 5 are superimposed. As is evident from FIG. 10(B), the waveforms were basically the same in the detection apparatus of Comparative Example 5 in which no peptide was bonded to the through-hole, and flagellated *E. coli* and non-flagellated *E. coli* could not be identified.

[Identification of Influenza Virus, Molecule: Peptide]

Example 7

A device 1 and a detection apparatus 1-1 were produced by the same procedure as in Example 5 except that the following three types of peptides designed to recognize influenza viruses were used instead of SEQ ID NO: 2.

ASHRVGSTYIAGGGC (SEQ ID NO: 3)

ASHRVGSTYIGGGC (SEQ ID NO: 4)

RVGSTYGGGC (SEQ ID NO: 5)

Example 8 (with Molecule) and Comparative Examples 6 and 7 (without Molecule)

Next, the ion current was measured by the same procedure as in Example 6 except that the detection apparatus produced in Example 7 and Comparative Example 4 were used and samples were prepared by the procedure described below using influenza A virus [influenza A virus (H1N1), A/PR/8/34 (American Type Culture Collection, VR-95) and influenza B virus (influenza B virus, B/Lee/40 (American type Culture Collection, VR-1535)].

<Virus Preparation Method>

The viruses were cultured by a conventional method in embryonated eggs. Specifically, after inspecting eggs cultured while turning at 37° C. and relative humidity of 60% or higher in an incubator, the influenza virus was inoculated into the chorioallantoic membrane and cultured for another three days. The eggshell membrane was broken from the air chamber, and the chorioallantoic fluid was collected by aspiration.

Figure 11:
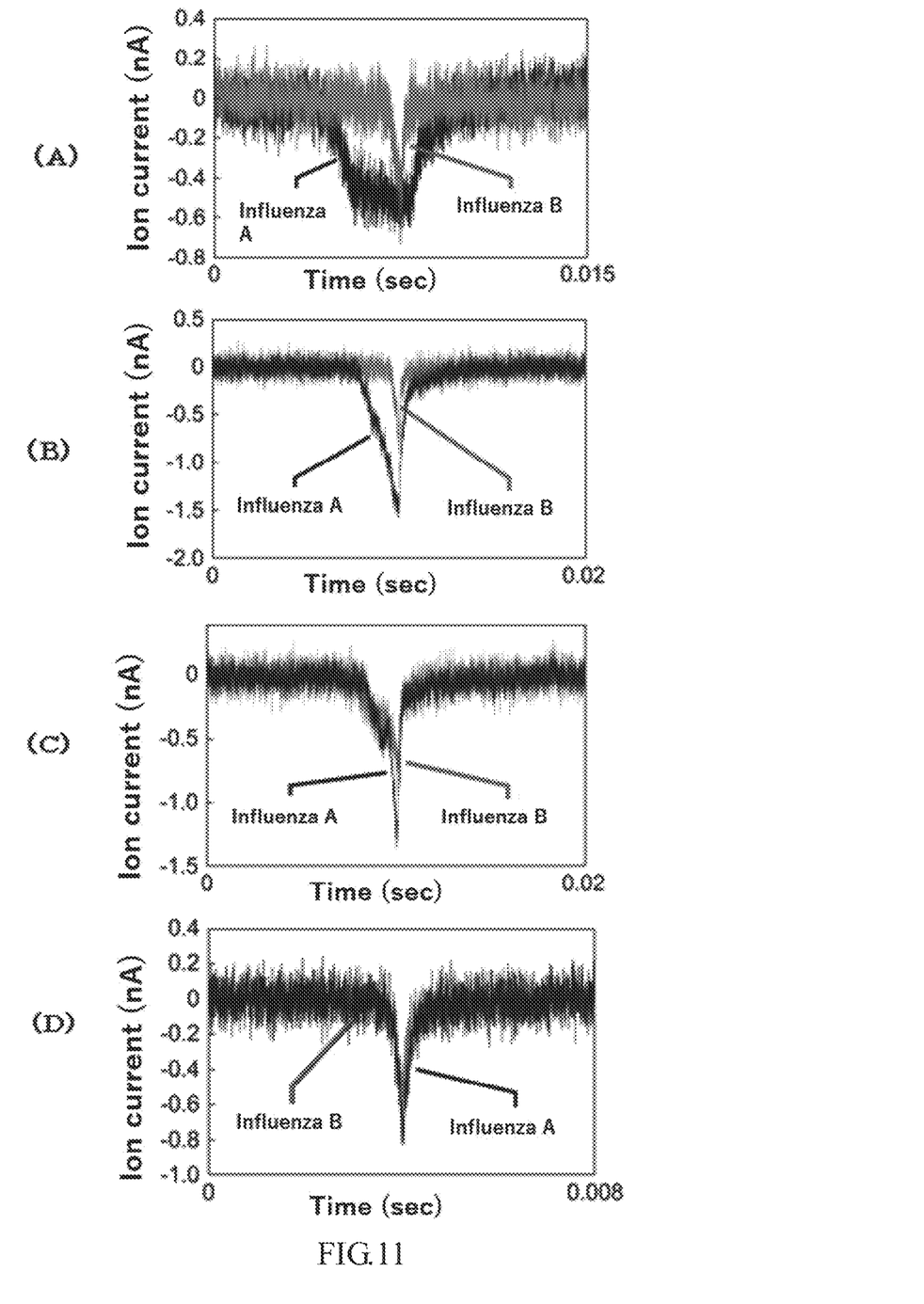

FIG. 11(A) for a molecule of SEQ ID NO: 3, FIG. 11(B) for a molecule of SEQ ID NO: 4, and FIG. 11 (C) for a molecule of SEQ ID NO: 5 are graphs in which waveforms of ion currents of one sample each are superimposed. As is evident from FIG. 11(A)-(C), influenza A and B viruses could be identified in Example 8 in which a peptide designed to recognize the influenza virus was bonded to the through-hole. Also, it was confirmed that the waveforms of the ion current measured differ greatly due to differences in the peptide sequence. In Comparative Example 6 in which no peptide was bonded, the influenza virus adsorbed around the through-hole, and the ion current could not be measured. Furthermore, gold vapor deposition is thought to be the reason that the influenza virus adsorbed around the through-hole. A detection apparatus in which the through-hole diameter was set at 300 nm and no gold was vapor deposited and no molecule was bonded was therefore produced based on the procedures described in Examples 1 and 2, and the ion current was measured (Comparative Example 7). FIG. 11(D) is a graph in which waveforms of ion currents of one sample each in Comparative Example 7 are superimposed. As shown in FIG. 11(D), the influenza virus could not be identified when a through-hole was simply formed. Based on the above results, not only could the influenza virus be identified, but the influenza virus could be measured by bonding an interacting molecule to the through-hole.

[Identification of Influenza Virus, Molecule: Sugar Chain]

Example 9

A device 1 and a detection apparatus 1-1 were produced by the same procedure as in Example 5 except that the following sugar chain (6'-sialyllactose, manufactured by Tokyo Chemical Industry Co., Ltd.) was bonded to the through-hole by the following bonding method.

<Bonding Method>

Undecane disulfide having an oxylamino group ($H_2N-O-(CH_2)_{11}-S-S-(CH_2)_{11}-OH$, $H_2N-O-(CH_2)_{11}-S-S-(CH_2)_{11}-NH_2$) (0.1 mmol/L) was synthesized using the document of Park et al. (Langmuir, 2008, Vol. 24, 6201-6207) as a reference. The material for forming an intermediate layer obtained was dissolved in ethanol, and a solution for forming a self-assembled monolayer (SAM) was prepared. A through-hole having a layer of gold was immersed in the solution for SAM formation, and an SAM to immobilize the sugar was formed by standing for one hour. The sugar was prepared in a concentration of 0.1 mmol/L in pH 5.3 acetic acid solution, and the sugar was immobilized by immersing the through-hole for 15 minutes.

[Chemical formula 1]

Example 10 (with Molecule) and Comparative Example 8 (without Molecule)

Next, the ion current was measured by the same procedure as in Example 6 using the detection apparatus produced in Example 9 and Comparative Example 4 and using detoxified influenza virus as the sample. Furthermore, the detoxified influenza virus was prepared by the procedure described below.

<Method for Preparing Detoxified Influenza Virus>

A solution containing detoxified influenza A virus H1N1 (HA titer 256) was prepared by 0.05% paraformaldehyde solution as a stock solution of the specimen solution.

Figure 12:
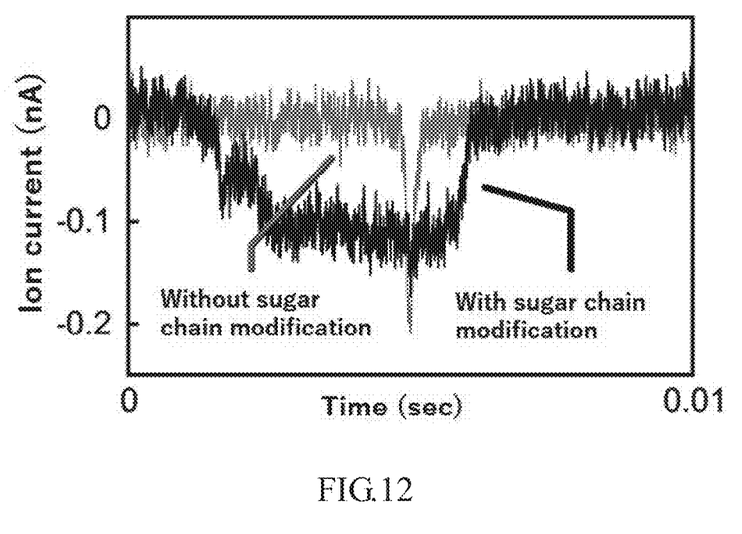
FIG. 12 is a graph in which waveforms of ion currents measured in Example 10 and Comparative Example 8 are superimposed.

FIG. 12 is a graph in which waveforms of ion currents of one sample each measured in Example 10 and Comparative Example 8 are superimposed. As is evident from FIG. 12, when the ion current value (Ip) was measured by the detection apparatus of Example 9 in which the sugar chain that recognizes the influenza virus was bonded to the through-hole, the waveform clearly differed from that of the ion current value measured by the detection apparatus of Comparative Example 4 in which no sugar chain was bonded. Therefore, it was clear that the influenza virus could be identified by bonding the sugar chain to the through-hole.

Other Embodiments

In addition, the following embodiments of a device for sample detection, a sample detection apparatus, an ion current detection method, and a sample identification method may also be adopted in the present invention. In addition, these may be combined as is appropriate with the embodiments given as examples above.

(1) A device for sample detection including
a substrate,
a through-hole through which a sample passes, the through-hole being formed in the substrate, and
a molecule formed in the through-hole, the molecule interacting with the through-passing sample.

(2) The device for sample detection according to (1) above in which the interacting molecule is a peptide or a nucleic acid.

(3) The device for sample detection according to (1) or (2) above in which a metal layer is laminated in the through-hole and the interacting molecule is formed on the metal layer.

(4) The device for sample detection according to any of (1)-(3) above including
a first chamber member that forms, with at least the surface including the through-hole on one surface side of the substrate, a first chamber to be filled with electrolyte and
a second chamber member that forms, with at least one surface including the through-hole on the other surface side of the substrate, a second chamber to be filled with electrolyte.

(5) A sample detection apparatus including
the device for sample detection according to (4) above,
a first electrode formed in the first chamber,
a second electrode formed in the second chamber, and
an ammeter for measuring the ion current when the sample passes through the through-hole.

(6) A method for measuring an ion current in which a measurement is made of the ion current when a sample passes through a through-hole formed in a substrate wherein a molecule that interacts with the sample is formed in the through-hole and the sample passes through the through-hole while interacting with the molecule, whereby the time it takes the sample to pass through the through-hole is increased.

(7) The method for measuring an ion current of (6) above wherein the interacting molecule is a peptide or a nucleic acid.

(8) A sample identification method for identifying a sample from the ion current measured by the method for measuring an ion current according to (6) or (7) above.

INDUSTRIAL APPLICABILITY

Even samples of basically the same size can be identified by using the device 1 of the present invention. Therefore, the device is useful in the development of detection apparatus since it can be used as a measurement unit of a detection apparatus of an instrument for measuring an ion current.

What is claimed is:

1. A device for biological material detection comprising:
a substrate;
a through-hole through which a biological material to be tested passes, the through-hole being formed in the substrate; and
an interacting molecule that interacts with the biological material to be tested, the interacting molecule being formed in the through-hole,
wherein the interacting molecule is formed in one of manners selected from following (1) to (3):
(1) a metal layer is laminated in the through-hole and the interacting molecule is formed on the metal layer,
(2) an amino group or carboxyl group of the interacting molecule is bonded to the through-hole, and
(3) the through-hole is covered by polyurethane, and the interacting molecule having modified polydopamine as a scaffold is bonded to a surface of the polyurethane,
a type of the biological material to be tested is identified by an analysis, by an analysis unit, of a waveform of an ion current generated when the biological material to be tested passes through the through-hole, and
the interacting molecule is an influenza-recognizing peptide consisting of SEQ ID NO: 4.

2. The device for biological material detection according to claim 1, further comprising:
a first chamber member that forms, with at least a surface including the through-hole of one surface side of the substrate, a first chamber to be filled with electrolyte; and
a second chamber member that forms, with at least a surface including the through-hole on another surface side of the substrate, a second chamber to be filled with the electrolyte.

3. The device for biological material detection according to claim 1, wherein:
the substrate is formed by an insulating material,
the metal layer is formed on the substrate,
an insulating layer is formed on the metal layer, and
the interacting molecule is formed on the metal layer exposed in the through-hole.

4. The device for biological material detection according to claim 2, wherein:
the substrate is formed by an insulating material,
the metal layer is formed on the substrate,
an insulating layer is formed on the metal layer, and
the interacting molecule is formed on the metal layer exposed in the through-hole.

5. The device for biological material detection according to claim 1, wherein the biological material to be tested is one or more of bacteria, viruses, DNA, and proteins.

6. A detection apparatus for biological material detection including:
the device for biological material detection according to claim 2;
a first electrode formed in the first chamber;
a second electrode formed in the second chamber;
an ammeter for measuring the ion current; and
a controller and a memory storing a program, as the analysis unit,
wherein the program, when executed by the controller, causes the controller to identify the type of the biological material to be tested.

7. A detection apparatus for biological material detection including:
the device for biological material detection according to claim 4;
a first electrode formed in the first chamber;
a second electrode formed in the second chamber;
an ammeter for measuring the ion current; and
a controller and a memory storing a program, as the analysis unit,
wherein the program, when executed by the controller, causes the controller to identify the type of the biological material to be tested.

8. The device for biological material detection according to claim 1, wherein the metal layer is laminated only to the through-hole.

9. The detection apparatus according to claim 6, wherein:
the detection apparatus includes a controller and a memory storing a program, as the analysis unit, and
the program, when executed by the controller, causes the controller to analyze an ion current change time and the waveform of the ion current from a timing that the biological material enters the through-hole to a timing that the biological material exits from the through-hole and measured by the ammeter, to identify the type of the biological material to be tested.

* * * * *

SEQUENCE LISTING

```
<160> NUMBER OF SEQ ID NOS: 5

<210> SEQ ID NO 1
<211> LENGTH: 12
<212> TYPE: PRT
<213> ORGANISM: Artificial Sequence
<220> FEATURE:
<223> OTHER INFORMATION: synthesized

<400> SEQUENCE: 1

Gly Arg His Ile Phe Trp Arg Arg Gly Gly Gly Cys
1               5                   10

<210> SEQ ID NO 2
<211> LENGTH: 12
<212> TYPE: PRT
<213> ORGANISM: Artificial Sequence
<220> FEATURE:
<223> OTHER INFORMATION: synthesized

<400> SEQUENCE: 2

Phe Leu Leu Arg Val Pro His Leu Gly Gly Gly Cys
1               5                   10

<210> SEQ ID NO 3
<211> LENGTH: 15
<212> TYPE: PRT
<213> ORGANISM: Artificial Sequence
<220> FEATURE:
<223> OTHER INFORMATION: synthesized

<400> SEQUENCE: 3

Ala Ser His Arg Val Gly Ser Thr Tyr Ile Ala Gly Gly Gly Cys
1               5                   10                  15

<210> SEQ ID NO 4
<211> LENGTH: 14
```

-continued

```
<212> TYPE: PRT
<213> ORGANISM: Artificial Sequence
<220> FEATURE:
<223> OTHER INFORMATION: synthesized

<400> SEQUENCE: 4

Ala Ser His Arg Val Gly Ser Thr Tyr Ile Gly Gly Gly Cys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: synthesized

<400> SEQUENCE: 5

Arg Val Gly Ser Thr Tyr Gly Gly Gly Cys
1               5                   10
```